United States Patent [19]

Schneider

[11] Patent Number: 4,982,736
[45] Date of Patent: Jan. 8, 1991

[54] HERMAPHRODITIC COUPLING FOR ANATOMICAL THERMAL SYSTEM

[75] Inventor: Barry L. Schneider, Deerfield, Ill.

[73] Assignee: Hollister Incorporated, Libertyville, Ill.

[21] Appl. No.: 308,312

[22] Filed: Feb. 8, 1989

[51] Int. Cl.$^5$ .......................... A61F 7/00; F16K 51/00
[52] U.S. Cl. ..................................... 128/400; 604/249; 165/46; 137/614.04; 251/149.7
[58] Field of Search ............... 604/113, 114, 283, 291, 604/293, 308, 249; 606/27, 28; 128/24.1, 68.1, 399–403; 165/46; 285/131, 137.1, 330, 334.4, 921; 403/339, 340; 137/614.04, 595, 871; 251/149.6, 149.7

[56] References Cited

U.S. PATENT DOCUMENTS

| | | | |
|---|---|---|---|
| 418,408 | 12/1889 | Graver | 285/334.4 |
| 488,717 | 12/1892 | Pettet | 137/614.04 |
| 719,633 | 2/1903 | Batter | 604/293 |
| 1,239,345 | 9/1917 | Brown | 251/149.7 |
| 2,819,914 | 1/1958 | Eitner | 285/330 |
| 3,577,105 | 5/1971 | Jones, Jr. | 403/339 |
| 4,010,795 | 3/1977 | Stenberg | 165/46 |
| 4,694,859 | 9/1987 | Smith, III. | 251/149.7 |
| 4,706,847 | 11/1987 | Sankey et al. | 137/614.04 |
| 4,753,268 | 6/1988 | Palau | 251/149.6 |

FOREIGN PATENT DOCUMENTS 1442777  5/1966  France ............... 137/614.04

Primary Examiner—Stephen C. Pellegrino
Assistant Examiner—Ralph Lewis
Attorney, Agent, or Firm—Tilton, Fallon, Lungmus

[57] ABSTRACT

A hermaphroditic coupling especially useful in an anatomical thermal system between the pad means and control unit thereof, the hermaphroditic coupling including a pair of parallel lumens with the coupling being divided into two units having identical hermaphroditic, engageable ends and with releasable latch means connecting the two elements of the hermaphroditic coupling.

11 Claims, 2 Drawing Sheets

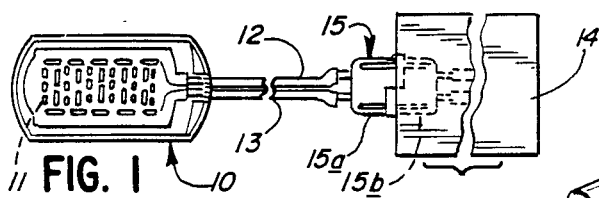
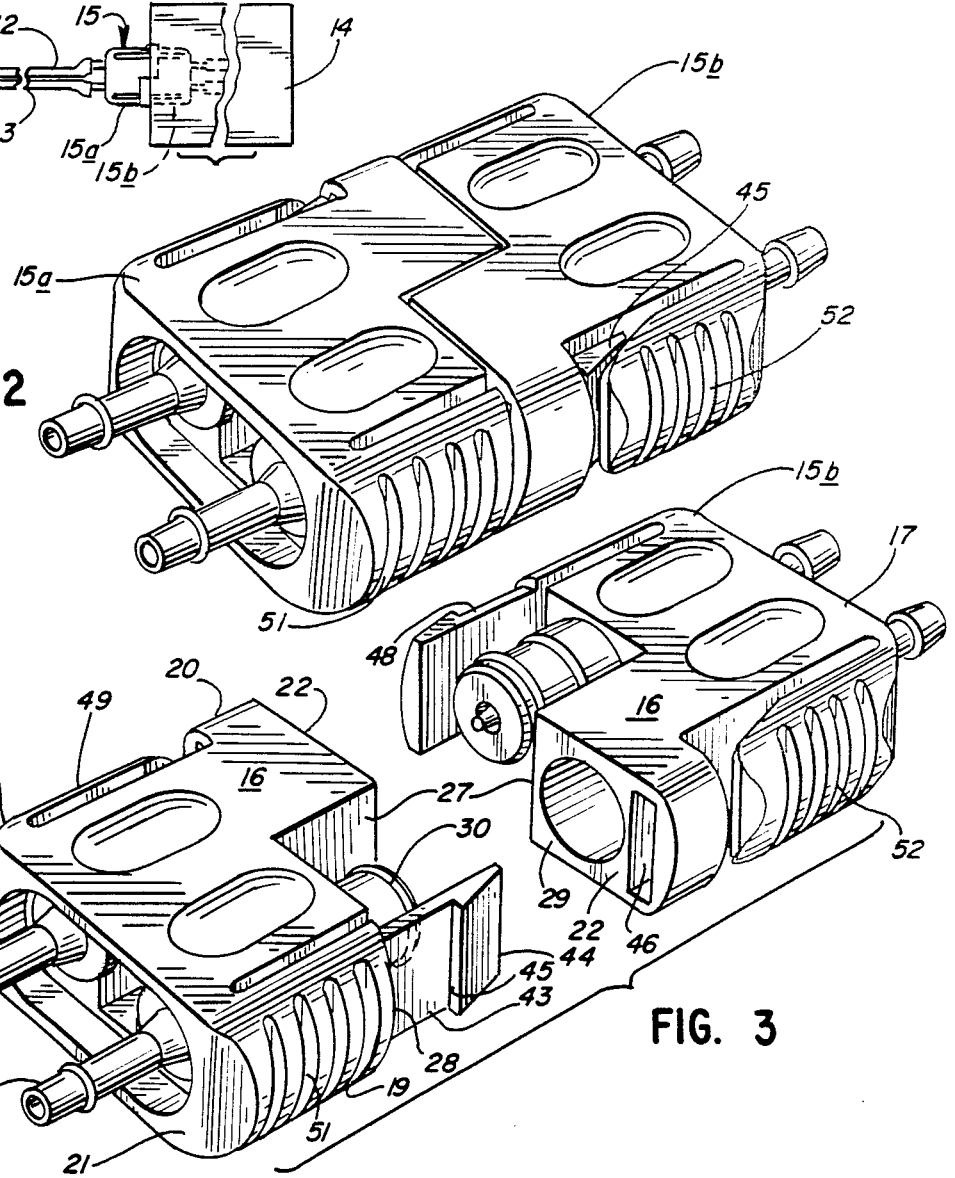
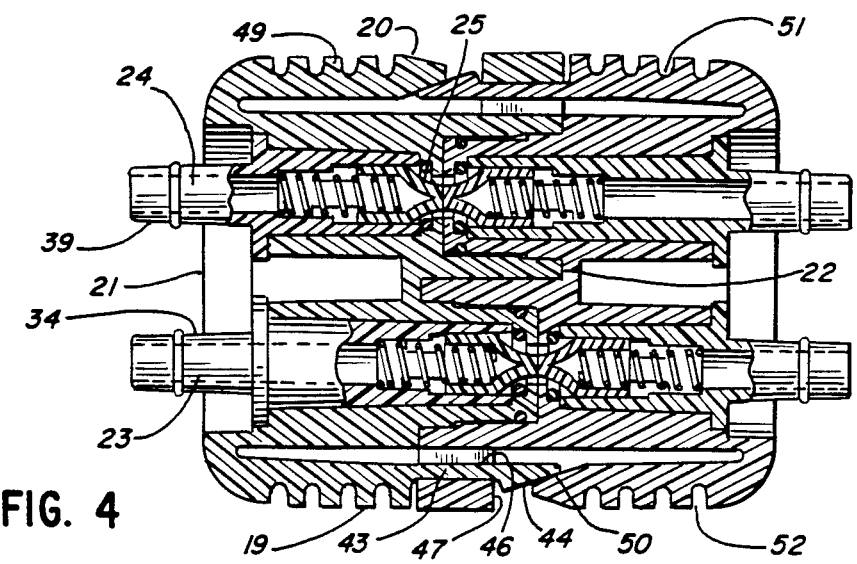

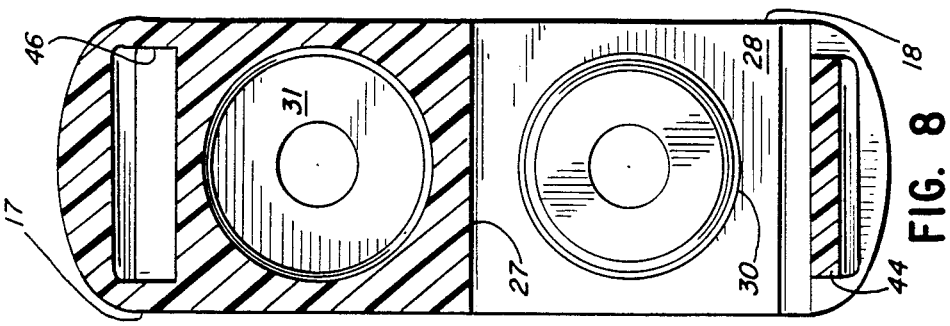
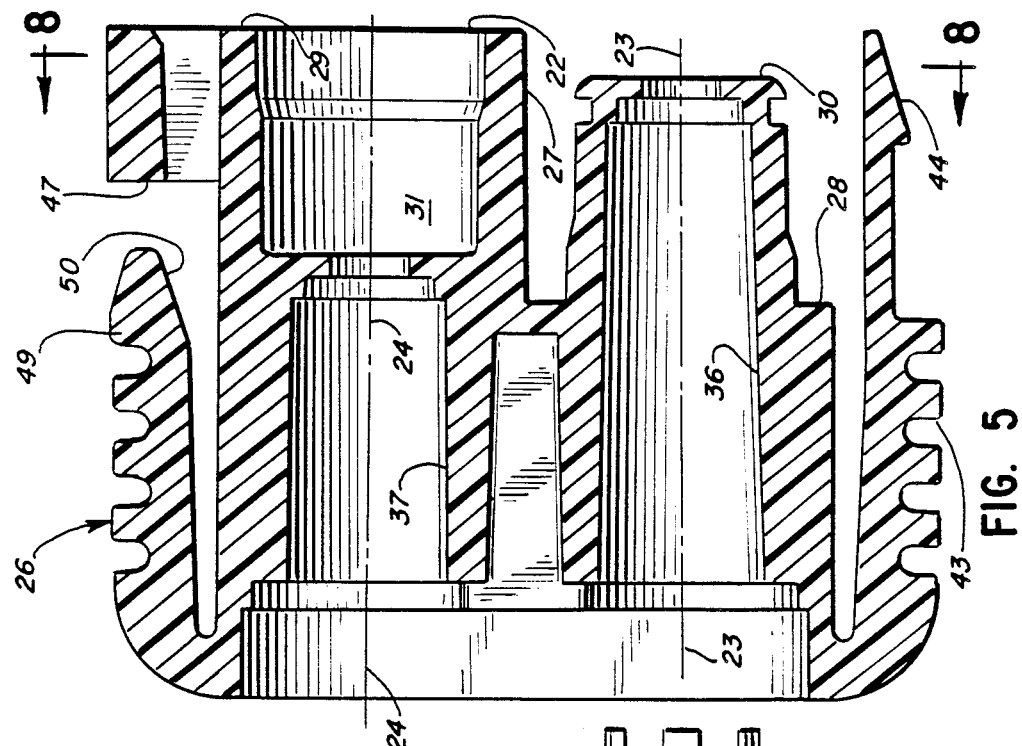
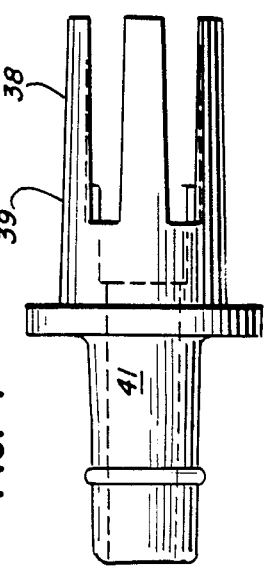
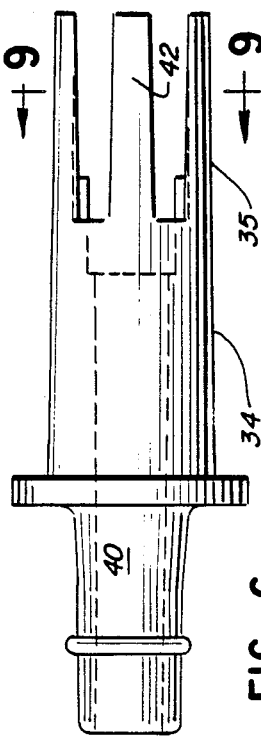
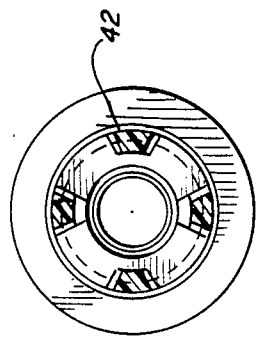

HERMAPHRODITIC COUPLING FOR ANATOMICAL THERMAL SYSTEM

BACKGROUND AND SUMMARY OF INVENTION

This invention relates to a hermaphroditic coupling or connector useful in an anatomical thermal system and, more particularly, to the type of system employing two tubes for the conduction of the thermal fluid, i.e., for heating or cooling.

There has been widespread use of thermal pads for placement on the body of a patient so as to either heat or cool the area contacted. The pad is connected by supply and return tubing to a control mechanism which usually includes a pump or other prime mover. In the past, there have been instances of mis-connection whereby the return line was connected to the supply side and vice versa resulting in the need for readjustment. This significant drawback is avoided by the teachings of the instant invention.

The instant invention makes use of a pair of connecting elements having hermaphroditic ends, i.e., both male and female, which results in error-proof connection and operation. Additionally, the invention provides a novel squeezable latching means for releasably connecting together the two hermaphroditic elements.

Other objects and advantages of the invention may be seen in the details of the ensuing specification.

The invention is explained in conjunction with an illustrative embodiment in the accompanying drawing, in which—

FIG. 1 is a schematic view of a typical hospital installation featuring the use of the invention;

FIG. 2 is an enlarged fragmentary perspective view of the coupled hermaphroditic elements of the invention;

FIG. 3 is a view similar to FIG. 2 but with the hermaphroditic elements separated so as to more clearly delineate the structural features of the hermaphroditic ends of the two elements;

FIG. 4 is a longitudinal sectional view of the coupled elements;

FIG. 5 is a sectional view of the generally block-like body of each element;

FIGS. 6 and 7 are side elevational views of adapters introduced into the body of FIG. 5 so as to provide the connections to tubing away from the hermaphroditic end thereof;

FIG. 8 is a sectional view seen along the sight line 8—8 applied to FIG. 5; and

FIG. 9 is a section view taken along the sight line 9—9 applied to FIG. 6.

DETAILED DESCRIPTION

Referring to FIG. 1, the numeral 10 designates generally pad means of the nature used in thermal treatment of patients by application to the body and which is usually equipped with interior conduit means shown schematically as at 11. Supply tubing or conduit means for the thermal fluid (hot/cold) is provided at 12 and the return line at 13. These lines are coupled to a control unit 14 by means of a hermaphroditic connector or coupling 15. More particularly, the coupling 15 includes elements 15a and 15b which, in the illustration given are identical. The important aspect is that the connected ends, i.e., the hermaphroditic ends, be identical because where the element 15b is mounted on or in the control unit 14, the end opposite to the hermaphroditic end may be varied somewhat. However, for ease of presentation and understanding, the invention will be described in connection with elements 15a and 15b that are identical. These can be seen in larger scale in FIG. 2 and in greater detail insofar as the hermaphroditic ends are concerned, in FIG. 3.

Referring now to FIG. 3, each of the elements 15a and 15b consist of a block-like body 16. The body 16 has a top wall 17 and a bottom or lower wall 18—see FIG. 8. In the illustration given, these walls are substantially planar and are flanked by sidewalls 19 and 20—see also FIG. 4. Finally, each body 16 is defined by end walls, one end wall being remote from the hermaphroditic coupling being designated 21 and the end wall carrying the hermaphroditic elements being designated 22—see particularly the element 15b at the right hand portion of FIG. 3.

Each element 16 has a pair of longitudinally extending lumens therein as can be readily appreciated from the elements designated 23 and 24 at the left hand portion of FIG. 4. The first and second lumens 23, 24 can be considered to be essentially longitudinally extending and further extend from one end 21 of the body 16 to the other end 22 so as to provide a through passage for the thermal fluid. Each lumen in each element is equipped with a check valve as at 25 in the upper left hand portion of FIG. 4. Check valves in the nature of poppets are conventional in thermal treatment systems and, therefore, a wide variety of specific designs are available for the person skilled in the art practicing the instant invention.

Reference is now made to FIG. 5 where the numeral 26 designates generally the basic component of the body 16. The showing in FIG. 5 is essentially that of the element 15a—i.e., with the hermaphroditic end 22 being to the right.

The end wall 22 is seen to be stepped as at 27—compare FIG. 5 with the central portions of FIG. 3. This divides the wall 22 into a first portion 28 which is positioned closer to the end wall 21 than the second portion 29—for convenience compare the right hand portion of FIG. 3.

Referring again to FIG. 5, the step 27 is seen to be positioned along the longitudinal midplane of the body 16 or 26 and thus lies between the axis of the first lumen 23 and the axis of the second lumen 24.

Extending longitudinally away from the first portion 28 is a male projection 30 which is aligned with the first lumen 23. Extending inwardly, i.e., toward the end wall 21 from the end wall 22, is a recess 31 in the second portion 29. The interior contour of the recess 31 conforms to the external contour of the projection 30 and, in effect, is also a continuation of the second lumen 24.

Referring again to FIG. 3, it will be seen at the extreme left hand portion thereof that there are a pair of coupling elements 32 and 33 which couple the first and second lumens 23, 24 to the tubes 13, 12, respectively. These are advantageously provided in the form of adapters which are seen in FIGS. 6 and 7. The adapter of FIG. 6 is designated 34 and is seen to include a first end 35 which is relatively tapered so as to fit within the relatively tapered bore 36 of the body 26—see FIG. 5. The body 26 is also equipped with a second tapered bore 37 which receives the first portion 38 of the adapter 39 associated with the second lumen 24. This is shorter in extent than the tapered portion 35 due to the difference in length of the bores 36, 37. Outboard of the tapered portions 35, 38, the adapters 34, 39 are identical in providing second portions 40, 41 for the ensleeving receipt of the tubes 13, 12, respectively. It is advantageous to provide the tapered portions in the form of split fingers 42 as illustrated also in FIG. 9 so as to facilitate assembly. These are the portions of the adapters 34, 39 which contain the poppet check valves 25—see FIG. 4.

Another advantageous feature of the invention is the provision of squeezable latching means coupling the elements 5a, 15b. These again are essentially male and female as can be appreciated from a consideration of FIGS. 3 and 4.

Referring first to FIG. 3, the numeral 43 designates an arm which extends longitudinally away from the first portion 28 of the end wall 22—and on the side of the projection 30 remote from the second lumen 24. It will be noted that the free end 44 of the arm 42 is equipped with a barbed portion 45 which passes through a passage 46—see FIG. 3 at the right hand end thereof—for snap engagement against an intermediate wall 47 (compare FIGS. 4 and 5). It will be appreciated that an identical arrangement is provided on the element 15b as can be appreciated from the arm 48 in the upper right hand portion of FIG. 3.

Provided in connection with the latching mechanism is a cam release feature which includes a second arm 49 also extending longitudinally but not quite as far as the arm 42. At its free end, the arm 49—see the upper central portion of FIG. 5 is equipped with a camming surface 50 which bears against the barb 44—see FIG. 4. Thus, squeezing of the arms 43 and 49 brings about a disengagement without the need for squeezing the element 15b which may be enclosed within the control unit 14.

Advantageously, the bodies 16 are constructed of resilient plastic material which, because of the relatively thin section of the arms 43, 49, can be flexed so as to perform the squeezing action just referred to. It is also advantageous to groove the exterior of the arms as at 51 and 52—see FIG. 2.

While in the foregoing specification a detailed description of an embodiment of the invention has been set down for the purpose of illustration, many variations in the details hereingiven may be made by those skilled in the art without departing from the spirit and scope of the invention.

I claim:

1. An element for a hermaphroditic type connector comprising a generally rectangular body defined by the top and bottom walls, a pair of end walls, a pair of longitudinally-extending lumens extending through said body from one end wall to the other, one each adjacent a sidewall, one of said end walls being equipped with coupling means aligned with said lumens for coupling the same to tubing means, the other of said end walls being equipped with a step between said lumens and defining first and second portions in said other end wall, said first portion of said other end wall being closer to said one end wall than said second portion, a hollow integral projection on said first portion and extending longitudinally away from said one end wall and aligned with a first of said lumens and providing a continuation of the same, and a longitudinally extending recess in said second portion aligned with the second of said lumens and providing a continuation of the same, said recess having an interior conforming to the exterior of said projection whereby an identical second element is adapted to be connected to said body, each lumen being equipped with a check valve openable by the connection of said second element to said body.

2. The structure of claim 1 in which at least one sidewall is equipped with releasable latch means for latching engagement with an identical second element.

3. The structure of claim 2 in which both said sidewalls are equipped with said releasable latch means, the latch means on a first of said sidewalls including a resilient barbed arm extending longitudinally away from said other end wall first portion and being located on the side of said projection remote from said second lumen, the latch means on the second of said sidewalls including a passage extending longitudinally from said second portion toward said one end wall and sized to receive a barbed arm on said second element conforming to the shape of the arm on said body, said passage being located on the side of said second lumen remote from said first lumen and terminating a spaced distance from said one end wall to provide an intermediate transverse wall for engagement with the barb on said second element arm.

4. The structure of claim 3 in which the latch means of the second of said side walls is equipped with cam means cooperable with the barb on the arm of said second element to unlatch the same from engagement with said intermediate transverse wall.

5. The structure of claim 4 in which said cam means includes a second arm of shorter length than the first mentioned arm.

6. The structure of claim 5 in which each arm is transversely grooved.

7. The structure of claim 2 in which said coupling means include a pair of tapered bores in said body aligned with said lumens and extending longitudinally from said one end wall partway toward said other end wall with the bore associated with said first lumen extending closer to said other end wall than the bore associated with said second lumen, said first lumen bore extending into said projection, and a hollow tubular adapter in each bore having a first longitudinally extending part conforming to its associated bore and a second part longitudinally extending beyond said one end wall to provide nipple means for coupling to said tubing means.

8. The structure of claim 7 in which said adapter second longitudinally extending parts have the same length.

9. An anatomical thermal system comprising pad means adapted to be positioned on the body of a patient and equipped with internal conduit for passage of thermal fluid, a temperature control mechanism spaced from said pad means and adapted to deliver and receive said thermal fluid, a pair of tubing means interconnecting said mechanism and pad means for separately delivering and returning said thermal fluid, and a coupling interposed in said tubing means, said coupling including a pair of elements having identical hermaphroditic ends in connected relation to each other, one of said elements being connected by said tubing means to said pad means and the other of said elements being connected to and communicating with said temperature control mechanism, each of said elements including a block-like body having a first and second longitudinally extending lumens therethrough, each body having one of said hermaphroditic ends, said hermaphroditic end of each body including a stepped end wall with a first wall portion being equipped with a longitudinally extending tubular projection aligned with said first lumen and a second wall recess aligned with said second lumen and sized to receive the tubular projection of the other body.

10. The structure of claim 9 in which said elements are equipped with latch means for releasably connecting said elements together.

11. The structure of claim 10 in which said latch means include a pair of longitudinally extending arms having free ends provided by each element, one arm being equipped with barb means at its free end and the other arm being equipped with cam means at its free end, the cam means of one element being operable to engage the barb means of the other element.

* * * * *